US005800435A

United States Patent [19]

Errico et al.

[11] Patent Number: 5,800,435
[45] Date of Patent: Sep. 1, 1998

[54] MODULAR SPINAL PLATE FOR USE WITH MODULAR POLYAXIAL LOCKING PEDICLE SCREWS

[75] Inventors: Joseph P. Errico, Far Hills; Thomas J. Errico, Summit; James D. Ralph, Oakland; Steven Tatar, Montville, all of N.J.

[73] Assignee: TechSys, LLC, Summit, N.J.

[21] Appl. No.: 846,473

[22] Filed: May 1, 1997

Related U.S. Application Data

[63] Continuation-in-part of Ser. No. 728,017, Oct. 9, 1996, and a continuation-in-part of Ser. No. 799,720, Feb. 12, 1997.

[51] Int. Cl.$^6$ ............................................. A61B 17/70
[52] U.S. Cl. ........................................... 606/61; 606/73
[58] Field of Search ............................... 606/61, 60, 72, 606/73, 69, 70, 71; 623/17

[56] References Cited

U.S. PATENT DOCUMENTS

| | | | |
|---|---|---|---|
| 5,053,036 | 10/1991 | Perren et al. | 606/69 |
| 5,209,751 | 5/1993 | Farris et al. | 606/61 |
| 5,290,288 | 3/1994 | Vignaud et al. | 606/61 |
| 5,429,639 | 7/1995 | Judet | 606/61 |
| 5,486,176 | 1/1996 | Hildebrand et al. | 606/71 |
| 5,527,315 | 6/1996 | Jeanson et al. | 606/61 |
| 5,584,887 | 12/1996 | Kambin | 623/17 |
| 5,591,166 | 1/1997 | Bernhardt et al. | 606/61 |
| 5,620,443 | 4/1997 | Gertzbein et al. | 606/61 |

*Primary Examiner*—Guy V. Tucker
*Attorney, Agent, or Firm*—Joseph P. Errico, Esq.

[57] ABSTRACT

A modular spinal plate assembly for use with modular polyaxial pedicle screw implant devices includes a track portion having a pair of parallel rails and a multiplicity of compressible coupling elements which are slideably mounted about the rails. The compressible coupling elements each have a through hole through which a post portion of a modular polyaxial screw may be mounted. In addition, the coupling elements include slots, oppositely oriented, on either side of the element, which slots may be compressed to effectuate the deflection and compaction of the coupling element when a compressive load is applied. This load is applied by a top locking nut being advanced along the post portion of the modular polyaxial pedicle screw, downwardly onto the coupling element. The subsequent compaction causes the coupling element to be compression locked to the rails, thereby becoming rigidly fixed at a specific position along the axial extent of the track element. Multiple post portions of sequential pedicle screws are coupled to the same track element via multiple coupling elements to effectuate the relative immobilization of a sequence of vertebral bones.

7 Claims, 5 Drawing Sheets

MODULAR SPINAL PLATE FOR USE WITH MODULAR POLYAXIAL LOCKING PEDICLE SCREWS

CROSS-REFERENCE TO PRIOR APPLICATION

This is a continuation-in-part of applications U.S. Ser. Nos. 08/728,017 filed Oct. 9, 1996, still pending, and 08/799,720, filed Feb. 12, 1997, still pending, each entitled "A Modular Polyaxial Pedicle Screw".

BACKGROUND OF THE INVENTION

1. Field of the Invention

This invention relates generally to a spinal plating system for use with modular polyaxial pedicle screws. More particularly, the present invention relates to a modular plating assembly which receives modular polyaxial screws, and which may thereby be attached to the posterior or anterior-lateral surfaces of the vertebral column to immobilize the same.

2. Description of the Prior Art

The bones and connective tissue of an adult human spinal column consists of more than 20 discrete bones coupled sequentially to one another by a tri-joint complex which consist of an anterior disc and the two posterior facet joints, the anterior discs of adjacent bones being cushioned by cartilage spacers referred to as intervertebral discs. This structure houses and protects critical elements of the nervous system while also having innumerable peripheral nerves and circulatory bodies in close proximity. In spite of these complexities, the spine is a highly flexible structure, capable of a high degree of curvature and twist in nearly every direction. Genetic or developmental irregularities, trauma, chronic stress, tumors, and disease, however, can result in spinal pathologies which either limit this range of motion and/or threaten the critical elements of the nervous system housed within the spinal column. A variety of systems have been disclosed in the art which achieve this immobilization by implanting artificial assemblies in or on the spinal column.

These implant systems generally comprise multiple screws which are inserted into sequential vertebral bones, which screws are then rigidly coupled together with a rod or plate. It has been identified, however, that patient anatomy often necessitates the insertion of the screws at non-parallel relative alignments. If the heads of the screws are not flexible, it is correspondingly difficult to contour the rods or plates to seat on, or in the heads of the screws.

The art, therefore, contains a variety of attempts at providing instrumentation which purports to permit enhanced freedom for the surgeon with respect to aligning the screw and the rod. Most, however, are complex, inadequately reliable, and lack long-term durability. In addition, most generally lack the feature of being constructed to suit the specific anatomical requirements of every patient's spine. One system which has sucessfully achieved the ease of use and reliability necessary for superior surgical use is the Modular Polyaxial Screw designs disclosed in U.S. patent applications U.S. Ser. Nos. 08/728,017, and 08/799,720, each entitled "A Modular Polyaxial Pedicle Screw", the disclosures of each being hereby incorporated by reference.

It is, therefore, the principal object of the present invention to provide a modular plating system which may be utilized in conjunction with the above cited modular polyaxial pedicle screws and the like.

In addition, it is an object of the present invention to provide such a plating assembly which effectuates the reduction in surgical time necessary to contour rods and plates for use in spinal immobilization and fusion procedures.

Accordingly it is also an object of the present invention to provide plating system which is reliable, durable, and provides long term fixation support.

Other objects of the present invention not explicitly stated will be set forth and will be more clearly understood in conjunction with the descriptions of the preferred embodiments disclosed hereafter.

SUMMARY OF THE INVENTION

The preceding objects are achieved by the present invention which is a modular spinal plating system for use with modular polyaxial locking pedicle screws. More particularly, the spinal plating system comprises an elongate track, consisting of a pair of rails, spaced apart in parallel, coupled at each end. The rails slideably receive, thereabout, a multiplicity of compressible coupling elements. Each compressible coupling element comprises a first through hole into which the parallel rails are inserted in a manner which permits the coupling element to slide along the axial length of the track prior to it being compressed. A second through hole in the coupling element is provided so that it may receive the threaded shaft of a pedicle screw assembly (of the type set forth more specifically in U.S. Ser. Nos. 08/728,017 and 08/799,720, and as also set forth in summary hereinbelow).

In addition, the coupling elements each comprise a pair of slots on the outer lateral edges (the edges adjacent to, and laterally containing, the rails of the track element when same is inserted into the coupling element). The slots extend for more than half the axial length of the coupling element, and are directed in opposite directions. These slots permit the coupling element to deflect compressibly upon the application of a compressive force. This deflection causes the coupling element to rigidly lock to the rails.

In a preferred embodiment, the modular polyaxial screw comprises: a threaded shaft portion, which is inserted into the vertebral bone, the top of shaft portion including a bowl-shaped socket and a second threading; a stem portion having a threading for receiving a locking nut, the bottom of the stem portion being ball-shaped (a semi-spherical section); and a cylindrical locking cuff which is mounted about the ball-shaped bottom of the stem and threadably secured to the top of the shaft to secure the ball of the stem in the bowl-shaped socket of the shaft. Prior to complete tightening of the cuff, the stem is polyaxially coupled to the shaft. Tightening of the cuff causes the ball-shaped end of the stem to be compression locked in the bowl-shaped socket of the shaft.

In accordance with one surgical method which utilizes the present invention, a plurality of such polyaxial pedicle screws are implanted into the vertebral bone, and the stems are roughly positioned to receive the plating system and the cuffs are tightened, thereby locking the stems in place. The appropriate number of compressible coupling elements are then slideably advanced onto the track element (the track element itself may be sized according to the requirements of the surgeon). The coupling elements are aligned in accordance with the positions of the stems, and each of the the stems is then inserted through the second through hole of the corresponding compressible coupling element. It shall be understood that the rials and the openings in the coupling elements which comprise the second through holes are sufficiently contoured to receive stem portions which are not parallel to one another, and not perpendicular to the coupling element itself.

A top locking nut is then advanced along the threading of the stem until it contacts the top surface of the compressible coupling element. Continued downward force applied by the nut causes the slots of the coupling element to narrow, and the coupling element to deflect. This deflection causes the coupling element to lock to the rails of the track element, thus completely securing the assembly together.

BRIEF DESCRIPTION OF THE FIGURES

FIGS. 3a and 3b are top and side cross-section views, respectively, of a track element of the present invention, wherein the cross-section view of FIG. 3b is taken along line A—A of FIG. 3a;

DETAILED DESCRIPTION OF THE PREFERRED EMBODIMENT

While the present invention will be described more fully hereinafter with reference to the accompanying drawings, in which particular embodiments and methods of implantation are shown, it is to be understood at the outset that persons skilled in the art may modify the invention herein described while achieving the functions and results of this invention. Accordingly, the descriptions which follow are to be understood as illustrative and exemplary of specific structures, aspects and features within the broad scope of the present invention and not as limiting of such broad scope.

Figure 1C:
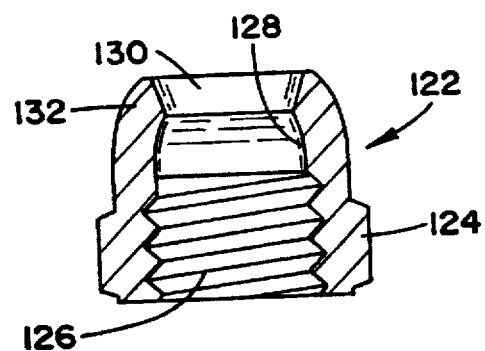
FIGS. 1a–c are side views of a threaded shaft, a stem portion, and a cuff element, respectively, which may be utilized in conjunction with the present invention (portions of FIG. 1a and all of FIG. 1c being in cross-section)
Figure 1B:
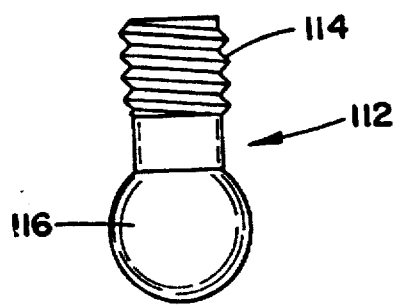
Figure 1A:
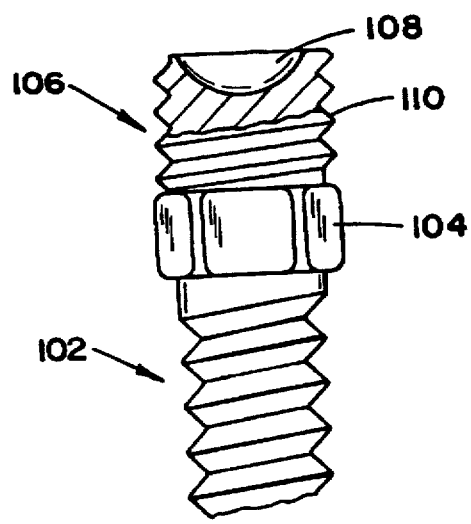

More particularly, referring now to FIGS. 1a–c, a modular polyaxial pedicle screw which may be used in conjunction with the present invention is provided. (A more complete description of this modular polyaxial pedicle screw and its alternative embodiments is provided in the above mentioned U.S. patent applications U.S. Ser. Nos. 08/728,017 and 08/799,720.) The shaft portion of this polyaxial screw is provided in FIG. 1a, and includes a threaded bone screw portion 102, a hexagonal midportion 104 (which is provided so that the shaft portion may be driven into the bone by convention hexagonal screw driving means), and an upper socket portion 106. The upper socket portion 106 includes a bowl-shaped upper end 108 and a threaded cylindrical exterior surface 110.

Referring now also to FIG. 1b, the stem portion 112 of this preferred modular polyaxial pedicle screw comprises an upper post portion 114, which is threaded, and a lower ball-shaped end 116 which has substantially the same radius of curvature as the bowl-shaped socket 108 of the shaft portion 102. This correspondence of shape permits the stem 112 to polyaxially rotate relative to the shaft 102 when the ball-shaped end 116 is seated loosely in the bowl-shaped socket 108.

Referring now also to FIG. 1c, the cuff portion 122 of the preferred embodiment comprises a cylindrical element having a lower portion 124 which comprises an interior threading 126 which mates with the threaded upper exterior cylindrical surface 110 of the shaft portion. The cuff 122 further includes an upper interior socket 128 in which the upper portion of the ball-shaped end 116 of the stem may 112 be held. The upper portion 132 of the cuff 122 includes an opening 130 through which the post portion 114 of the stem may extend (and polyaxially angulate relative to the cuff and shaft).

Figure 2:
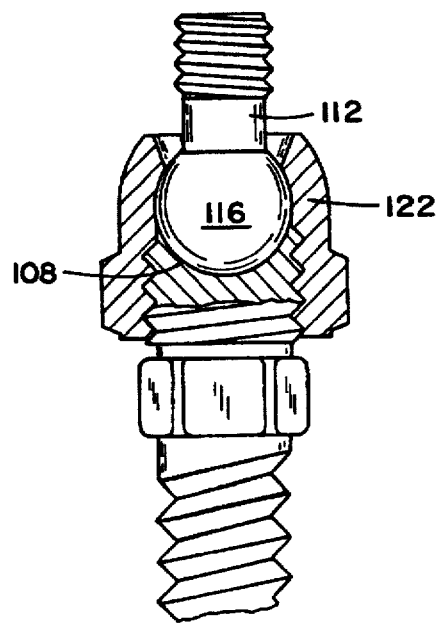
FIG. 2 is a partial cross-sectioned side view of an assembled polyaxial pedicle comprising the elements illustrated in FIGS. 1a–c.

Referring now also to FIG. 2, in which the assembled modular polyaxial pedicle screw is shown, it shall be understood that the tightening of the cuff 122 onto the threaded upper portion 110 of the threaded shaft portion causes the ball-shaped end 116 of the stem 112 to be locked in the bowl-shaped socket 108 of the shaft 102. Prior to tightening, the stem 112 may polyaxially float, so that the post may be roughly aligned with the posts of other similar polyaxial pedicle screws so that they may all receive thereon the plate system of the present invention.

Figures 3A, 3B:
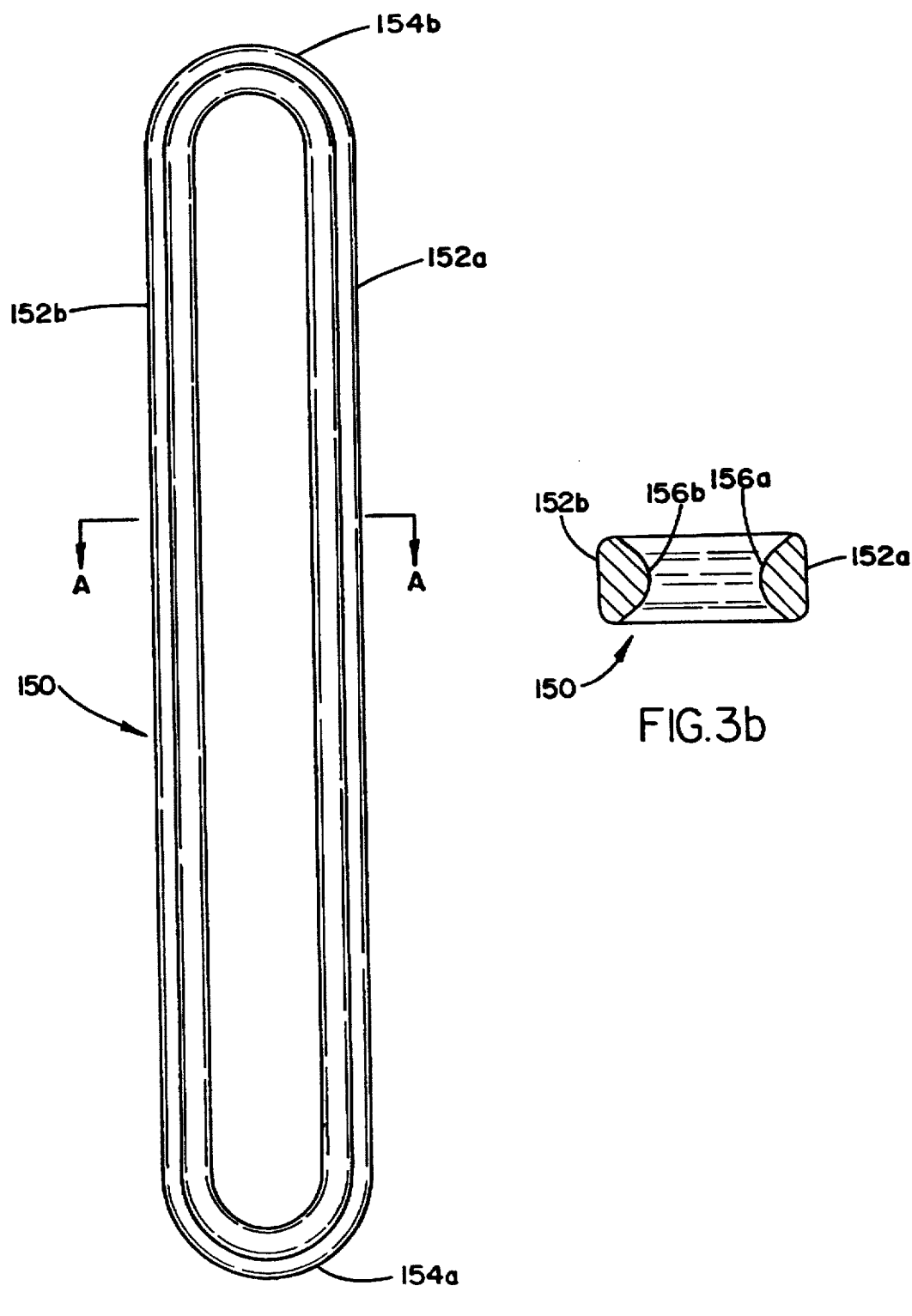

Referring now to FIGS. 3a and 3b, the track element of the present invention is shown in top and side cross-section views respectively. The side cross-section view of FIG. 3b is taken along line A—A of FIG. 3a. The track element 150 itself simply comprises a pair of rails 152a,152b which extend in a spaced apart relationship, parallel to one another for an axial length of the track. The ends 154a,154b of the track 150 comprise inwardly curved and contiguous ends of the rails 152a,152b such that the track maintains an elongated loop shape. Referring to FIG. 3b, the cross-section of the rails 152a,152b illustrated herein shows the curvate of the inwardly facing surfaces 156a,156b of the rails. This inward curvature is preferred insofar as it permits greater flexibility of coupling with a post portion 114 of a pedicle screw as it allows a range of entrance angles of the post 114 between the rails (described more fully hereinbelow).

Figure 4A:
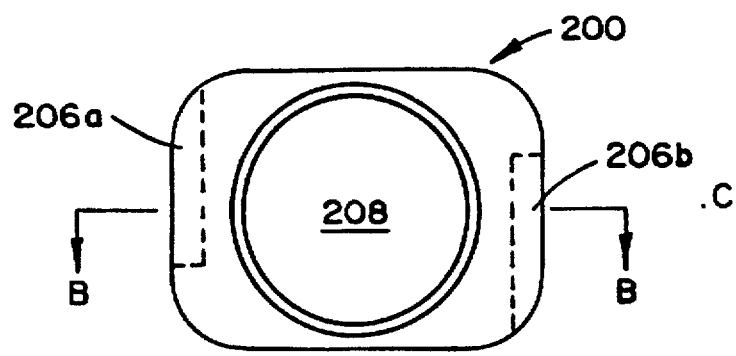
FIG. 4a is a top view of a compressible coupling element of the present invention.
Figure 4B:
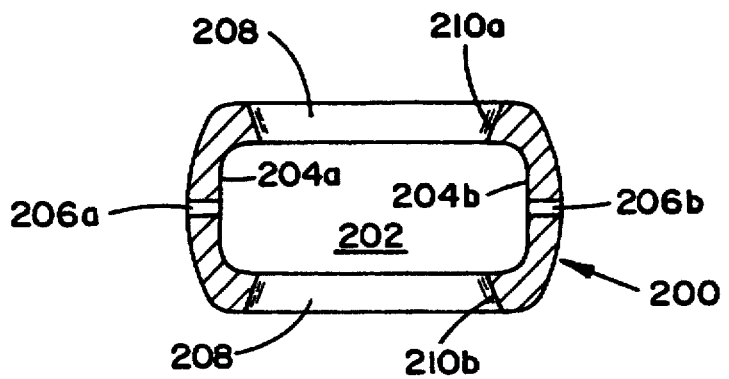
FIG. 4b is a side cross-section view of the compressible coupling element illustrated in FIG. 4a wherein said cross-section is taken along line B—B of FIG. 4a, and FIG. 4c is a side view of the compressible coupling element illustrated in FIG. 4a wherein the view is taken from point C.
Figure 4C:
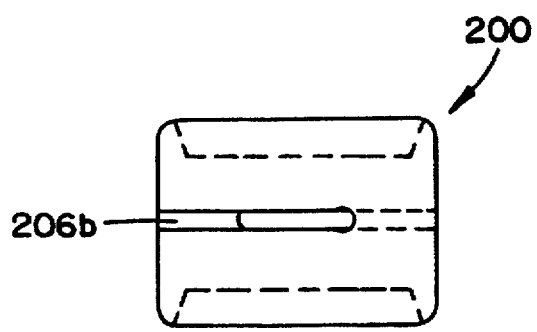

Referring now to FIGS. 4a–c, various views of the compressible coupling element 200 of the present invention are shown. More specifically with respect to the view of the coupling element provided in FIG. 4b, the element 200 comprises a hollow rectangular body, having a first through hole 202 which extends therethrough. This first through hole 202 is designed to receive the axial length of the track element 150. In particular, the lateral inner surfaces 204a, 204b are contoured to cup around the outer surfaces of the rails 152a,152b, respectively, such that the coupling element 200 may slide freely along the axial length of the track 150. In addition, the coupling element includes a pair of slots 206a,206b formed in the lateral walls 204a,204b, respectively. The slots 206a,206b do extend for more than half, but less than fully through the axial length of the coupling element 200, and are diagonally opposing in their orientation (see FIG. 4a).

Referring also to FIG. 4a, in which a top view of the compressible coupling element 200 is provided, the opposite sense of the incomplete slots 206a,206b is illustrated. A second through hole 208, extending through the upper and lower surfaces of the coupling element, is provided to receive the post 114 portion of a pedicle screw of the type illustrated and described with respect to FIGS. 1a–c and 2. The lips 210a,210b of the second through hole are tapered inwardly toward the hole in a manner which, like the taper of the inner surfaces 156a,156b of the rails, to permit easier coupling to non-perpendicularly received post portions 114. The embodiment shown in FIG. 4c is an alternative side view of the coupling element which illustrates the incomplete nature of the slots (slot 206b being shown).

Figure 5:
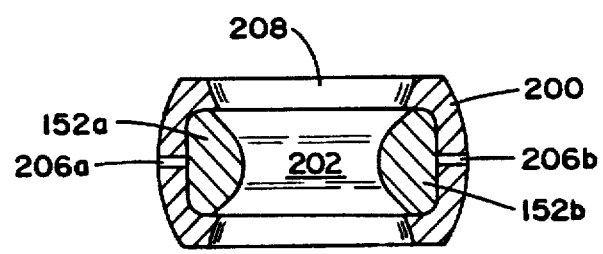
FIG. 5 is a side cross-section view of the initial position of the compressible coupling element illustrated in FIGS. 4a–c mounted about the track element illustrated in FIGS. 3a–b.

The coupling element 200 is designed to be compressibly compactible insofar as the application of a downward force on the coupling element 200 causes the slots 206a,206b to deflect, therein narrowing. This narrowing, if forced when the coupling element 200 is mounted to the rail, as illustrated in FIG. 5, causes the element to be compression locked to the rails 152a,152b. Therefore, the application of a sufficient compression force onto the compressible coupling element 200 when it is mounted to the track element 150 permits the two to be fully locked together (eliminating the slideability of the coupling element 200 relative to the axial extent of the track 150).

Figure 6:
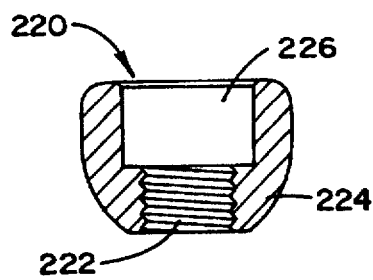
FIG. 6 is a side cross-section view of a top locking nut which may be utilized with the present invention.

Referring now to FIG. 6, the top locking nut 220 which is provided to be threadably engaged onto the threading of the upper post portion of the the stem 114 of the pedicle screw is shown in a side cross-section view. The inner portion of the nut has a threading 222, while the exterior surface 224 is curvately tapered to be received into the tapered second through hole 208 of the compressible coupling element 200 independent of the non-perpendicular entrance of the post portion 114 thereinto. The top of the locking nut 220 may also include a hexagonal recess 226, or other such screw driving tool receiving orifice, so that it may be advanced onto the threaded post portion 114.

Figure 7:
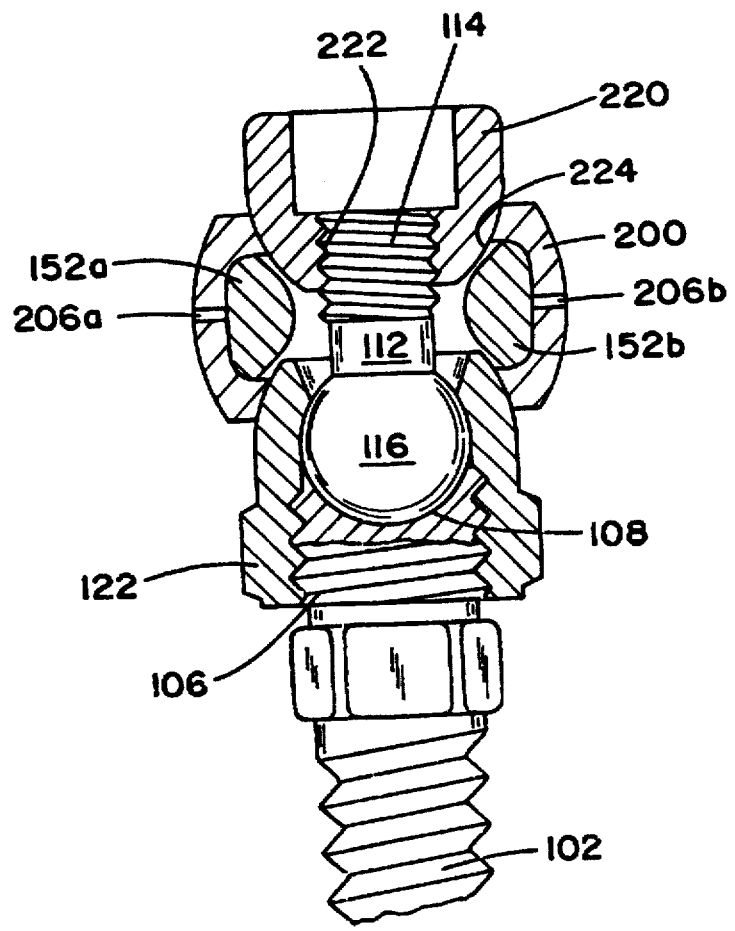
FIG. 7 is a partial cross-section side view of an embodiment of the present invention mounted to a fully assembled modular polyaxial locking screw comprised of the elements illustrated in FIGS. 1–6.

Referring now to FIG. 7, in which a fully assembled partial cross-section view of the pedicle screw and modular spinal plate is provided, the assembly and implantation procedure of the present invention is provided. First the shaft of the bone screw portion 102 is advanced into the appropriate pre-drilled in the vertebral bone of the patient. The stem 112 and cuff 122 of the pedicle screw are then coupled to the top portion of the shaft portion 102, such that the ball 116 is polyaxially seated into the socket recess 108 and is locked therein by means of the downward tightening of the cuff 122 onto the threads 106 thereof. In this position, the post portion 114 is rigidly locked into the polyaxial position desired by the surgeon. (It shall be understood that this polyaxial position includes angulations which are non-coaxial with the shaft and cuff portions as a result of the mutual engagement of the ball 116 and socket 108.)

The compressible coupling element 200 is then advanced into position along the rails 152a,152b of the track element 150. The threaded post portion 114 of the stem of the pedicle screw is then advanced through the second through hole 208 of the coupling element, until the upper portion of the cuff 122 seats into the tapered lower lip 210b of the coupling element 200. The top locking nut 220 is then threadably advanced onto the threaded post section 114 until the curvate bottom 224 of the nut seats in the upper opening of the second through hole 208, and against the upper lip 210a. Continued advancement of the top locking nut 220 causes a compressive force to be applied to the compressible coupling element 200. The applied load, which build between the fixed cuff 122 and the top locking nut 220, causes the incomplete slots 206a,206b to narrow, thereby causing the coupling element to be compression locked to the rails 152a,152b.

It shall be further noted that the advantage of having the coupling element 200 seat around the rails 152a,152b is to prevent the rails from expanding outwardly under the resultant (or any unforeseen) spreading force, such as the force of the top locking nut itself.

While there has been described and illustrated embodiments of a modular spinal plating system for use with polyaxial pedicle screws, it will be apparent to those skilled in the art that variations and modifications are possible without deviating from the broad spirit and principle of the present invention. The present invention shall, therefore, be limited solely by the scope of the claims appended hereto.

We claim:

1. A modular spinal plating assembly for use with spinal screws having post portions which are extendable above the surface of a vertebral bone into which it has been inserted, comprising:

a track element including a pair of parallel spaced apart rails;

at least one compressible coupling element including
a first through hole for receiving therethrough said parallel spaced apart rails,
a second through hole for receiving therethrough a corresponding one of said post portions of one of said spinal screws, said second through hole being capable of receiving said post portion within a range of angles relative to a perpendicular axis of said through hole, said range including non-zero angles, and
at least one slot, said slot being narrowable by the application of a compression force; and means for coupling said post portions to said corresponding at least one compressible coupling element, wherein said means for coupling is mounted on the corresponding post portion and includes a curvate contact surface for providing a downward force onto said compressible coupling element independent of the angle of said post portion relative to said perpendicular axis of said through hole of said compressible counting element, causing the narrowing of the at least one slot and the corresponding compression of the coupling element such that the coupling element is crush locked to the rails, and the corresponding pedicle screw and the plate assembly are rigidly locked together.

2. The assembly as set forth in claim 1, wherein the at least one slot of the at least one compressible coupling element comprises a pair of diagonally offset incomplete slots on opposite lateral portions thereof.

3. The assembly as set forth in claim 1, wherein the post portions further comprise threadings and the means for coupling each of said post portions to said corresponding compressible coupling element comprises a threaded top locking nut.

4. A modular polyaxial pedicle screw and plating assembly, comprising:

at least two pedicle screws having upper post portions, at least one of which including
a shaft having a lower portion and an upper portion, said upper portion having a threading thereon and a curvate socket formed in a top thereof,
a stem having one of said upper post portions and a lower ball portion, the ball portion being shaped to nest and initially rotate in said curvate socket, and
a cuff having an upper portion and a lower portion, said upper portion having an opening for receiving therethrough said upper post portion such that when the cuff is initially positioned on the shaft with the stem extending out from the opening in the cuff and the ball portion of the stem seated in the curvate socket of the shaft, the stem may polyaxially rotate relative to the shaft and cuff through a range of orientations including coaxial and non-coaxial ones, said lower portion having an interior threading which may be mated with the threading of the upper shaft portion, such that full advancement of the cuff onto the shaft causes the cuff, the shaft, and the stem to be locked together when the ball portion is crush locked in the curvate socket;

a plate assembly including a track element including a pair of parallel spaced apart rails, and a corresponding at least two compressible coupling elements each including a first through hole for receiving therethrough said parallel spaced apart rails, a second through hole for receiving therethrough said upper post portion of said stem of said pedicle screw, said second through hole being capable of receiving said upper post portion of said stem within a range of angles relative to a perpendicular axis of said through hole, said range including non-zero angles, and at least one slot, said slot being narrowable by the application of a compression force; and means for coupling said upper post portions to corresponding compressible coupling elements, said means being mountable to corresponding ones of said upper post portion of said stem and including a curvate contact surface, wherein the advancement of said means downwardly along the upper post portions, bringing said curvate contact surface into contact with the corresponding compressible coupling element independent of the angle of said upper post portion of said stem relative to said perpendicular axis of said through hole of compressible coupling element, causes the narrowing of the at least one slot of each coupling element and the corresponding compaction of the coupling element such that the coupling element is crush locked to the rails, and the pedicle screws and plate assembly are rigidly locked together.

5. The assembly as set forth in claim 4, wherein the at least one slot of the at least one compressible coupling element comprises a pair of diagonally offset incomplete slots on opposite lateral portions thereof.

6. The assembly as set forth in claim 4, wherein the post portions further comprise threadings and the means for coupling each of said post portions to said corresponding compressible coupling element comprises a threaded top locking nut.

7. A modular polyaxial pedicle screw and plating assembly, comprising:

at least two pedicle screws having threaded upper post portions, at least one of which including a shaft having a lower portion having a first threading thereon, and an upper portion having a second threading thereon and a curvate socket formed in a top thereof, a stem having said threaded upper post portion and a lower ball portion, the ball portion being shaped to nest and initially rotate in said curvate socket, and a cuff having a hollow cylindrical body having an upper portion and a lower portion, said upper portion having an opening having a diameter greater than that of the upper post portion and less than that of the ball portion such that when the cuff is initially positioned on the shaft with the stem extending out from the opening in the cuff and the ball portion of the stem seated in the curvature socket of the shaft, the stem may polyaxially rotate relative to the shaft and cuff through a range of orientations including coaxial and non-coaxial ones, said lower portion having an interior threading which may be mated with the second threading of the shaft portion, such that full advancement of the cuff onto the shaft causes the cuff, the shaft, and the stem to be locked together when the ball portion is crush locked in the curvate socket;

a corresponding at least two top locking nuts which are mateable with the threading on the post portions, said nuts having curvate contact surfaces; and a plate assembly including a track element including a pair of parallel spaced apart rails, and a corresponding at least two compressible coupling elements each including a first through hole for receiving therethrough said parallel spaced apart rails, a second through hole for receiving therethrough said stem portion of one of said pedicle screw, said second through hole being capable of receiving said stem within a range of angles relative to a perpendicular axis of said second through hole, said range including non-zero angles, and at least one slot, said slot being narrowable by the application of a compression force, wherein the advancement of the top locking nuts downwardly along the threaded upper post portions, into contact with the corresponding compressible coupling elements, independent of the angle of said stem relative to said perpendicular axis of said through hole of said compressible coupling element, causes the narrowing of the at least one slot of each coupling element and the corresponding compaction of the coupling element such that the coupling element is crush locked to the rails, and the pedicle screws and plate assembly are rigidly locked together.

* * * * *